United States Patent [19]

Herlihy

[11] Patent Number: 4,515,773
[45] Date of Patent: May 7, 1985

[54] SKIN TANNING COMPOSITION AND METHOD

[75] Inventor: Walter C. Herlihy, Cambridge, Mass.

[73] Assignee: Repligen Corporation, Cambridge, Mass.

[21] Appl. No.: 510,777

[22] Filed: Jul. 5, 1983

[51] Int. Cl.³ .......................... A61K 7/42; A61K 7/44; A61K 7/021
[52] U.S. Cl. .......................... 424/59; 424/60; 424/63; 514/785; 514/788
[58] Field of Search .............................. 424/60, 59, 63

[56] References Cited

U.S. PATENT DOCUMENTS 4,390,341  6/1983  Jacobs .................................... 424/60

FOREIGN PATENT DOCUMENTS 46-9158  3/1971  Japan .................................... 424/358

OTHER PUBLICATIONS

Riley, Journ. Society Cosmetic Chemistry, 1977, vol. 28, pp. 395 to 401.
Derwent Abstract No. 18183w/11 of Japanese Pat.-112642, 11/10/72, Shiseido.

Primary Examiner—Dale R. Ore
Attorney, Agent, or Firm—Roman Saliwanchik

[57] ABSTRACT

The subject invention concerns a novel, unobvious, and useful composition of matter and method for tanning the human epidermis. The composition comprises a suitable dye precursor and tyrosinase. These ingredients, when reacted together on the skin, result in the formation of melanin-like dyes which tan the skin.

6 Claims, No Drawings

SKIN TANNING COMPOSITION AND METHOD

DESCRIPTION

BACKGROUND OF THE INVENTION

The tanning of human epidermis by the sun's rays depends greatly upon the complexion of the individual. Persons with a fair complexion may have difficulty in obtaining a tan. Many such persons merely burn, and, thus, they must restrict their exposure to the sun. Despite the problems which may be encountered by some in obtaining a tan, there is a general desire to tan the skin for cosmetic reasons. Unfortunately, this desire can present serious medical problems for some individuals. Notable is the prevalence of skin cancers.

Obviously, where there is a tendency to burn rather than to tan under the sun's rays, it is desirable to screen out those rays. Accordingly, sunscreen compounds are also quite useful. Sunscreen products are based on compounds which absorb ultraviolet radiation in the range of 290–320 nm; therefore, these products prevent burning but do not promote tanning and offer only temporary protection.

In order to satisfy the cosmetic desires of individuals without incurring the undesirable effects of sun rays, there have been made available skin coloring products. Such products are typically based on dihydroxyacetone, which darkens the skin by interacting with the keratin in the stratum corneum. Although darkening can be achieved, a natural color is difficult to produce, and the color is not even and may be selectively removed by washing. Understandably, such products have not achieved market acceptance.

Though tanning of the human skin is motivated largely by cosmetic desires, it is also recognized that tanning, when done without detrimental burning, can have a protective effect on the skin. Thus there exists a need for a preparation to produce a natural-appearing tan which can protect the skin from potentially harmful radiation from the sun.

The commercially-available products for tanning and sunscreening, as noted above, have various limitations which militate against their extensive use. It should also be recognized that it is highly desirable that any compound or means for overcoming these limitations should also be non-mutagenic and non-allergenic since these are highly relevant and desired characteristics for any compound used on the human body.

BRIEF SUMMARY OF THE INVENTION

The subject invention provides a non-mutagenic, non-allergenic tanning composition which can be applied to the human epidermis to achieve a desired cosmetic effect and protect the skin from harmful sun rays. More specifically, the subject invention concerns the use of a novel enzymatic process for dyeing the human epidermis, and compositions which can be used in the process. Still more specifically, the subject invention concerns the use of the enzyme tyrosinase to catalyze the formation of melanin-like dyes on the human skin. The dyeing reaction can be initiated by mixing tyrosinase and a suitable dye precursor directly on the skin. Alternatively, the dye precursor and tyrosinase are in the same component but they are physically or chemically prevented from reacting. For example, tyrosinase can be sequestered by microencapsulation and released when the formulation is rubbed into the skin.

DETAILED DESCRIPTION OF THE INVENTION

As discussed above, tyrosinase is used to catalyze the formation of melanin-like dyes on the human skin by contact with suitable dye precursors. Suitable dye precursors are selected from the group consisting of tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3-methyl catechol, 3-isopropyl 6-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, O-cresol, m-cresol, p-cresol, or other related melanin precursors or analogs which are capable of being oxidized to tan, brown, or black compounds capable of dyeing the skin. Typically these precursors are present in a concentration range of about 10 mM to about 1M. Combinations of precursors can be used to control the color tone and intensity.

The enzyme catalyzing the formation of the melanin-like dye is tyrosinase (EC 1.14.18.1). Tyrosinase is present in the final reaction mixture at a concentration of about 50 to about 5000 U/ml. The pH of the solution is buffered with an acetate, phosphate, or other like buffer, to a pH of about 3 to about 10, preferably from about 5 to about 8.

The darkening of the human epidermis occurs approximately 1 to 3 mins. after application of a suitable composition comprising tyrosinase and a suitable dye precursor. Obviously, the actual time will vary with the individual and the extent of the application. These factors are easily determined by a person skilled in the art.

The intensity of the tan can be regulated by the concentration of tyrosinase and dye precursor in a single application, or by repeated applications of said composition. Further, organic solvents, e.g., ethanol and cetyl alcohol, and detergents, as exemplified herein, can be used to obtain desired color and intensity by means known in the art.

The dye precursor can be carried or suspended in various cosmetic bases suitable for external (topical) application directly to the human skin. For such application the base can take the form of liquid or cream lotions, ointments, and the like. The dye precursor can be used in varying concentrations, as discussed above, ranging from about 10 mM to about 1M.

Thus, a skin lotion can be prepared by mixing about 50% alcohol, 1% acetone, 45% water, and about 10 mM to about 1M of a dye precursor, as disclosed above. At the time of application of the lotion to the skin, a preparation of tyrosinase also can be applied to the skin and mixed with the aforementioned lotion containing the dye precursor.

An ointment can be prepared by methods well known in the art. For example, the dye precursor can be incorporated in an ointment base by mixing (by weight) 10.0 parts of glycerol monostearate, 10.0 parts of cetyl alcohol, 30 parts of spermaceti, 10.0 parts of Span 20 (sorbitan monolaurate), 10.0 parts of Tween 20 (polyoxylkylene derivative of sorbitan monolaurate), 12.5 parts of glycerin and 100 parts of water. The resultant ointment base can be compounded with an appropriate amount of the dye precursor as disclosed above. A thin coating of the ointment can be applied to the skin and mixed with a preparation of tyrosinase.

Various known sunscreening agents can be compounded with the dye precursors in a selected cosmetic base, for example, homomenthyl salicylate, butyl benzal acetone oxalate, acetanilide, benzyl salicylate, oxynaphthoic acid, dimethyl aminobenzoic acid, phenyl salicylate and the like, all of which function to filter out the actinic rays from the sun.

Further, it should be understood that the cosmetic base, in lotion, cream, or ointment form, can be variously compounded in accordance with the knowledge of those in the pertinent art to provide a suitable carrier or vehicle for the dye precursor and tyrosinase.

The above enabling examples of the embodiments of the subject invention can be varied by those skilled in the art without departing from the spirit of the subject invention. Thus, it should be understood that the examples given above are merely illustrative and not limiting except as set forth in the claims.

I claim:

1. A skin tanning composition which imparts color to the human epidermis which comprises a cosmetic base in the form of a lotion, a cream or an ointment, an effective amount of a dye precursor selected from the group consisting of tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxy-1,4-naphthaquinone (henna), 4-methyl catechol, 3-methyl catechol, 3-isopropyl 6-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, o-cresol, m-cresol, p-cresol, or other related melanin precursors or analogs which are capable of being oxidized to tan, brown, or black compounds capable of dyeing the skin distributed through said base, and an effective amount of tyrosinase.

2. A composition, according to claim 1, wherein said dye precursor is present at a concentration of about 10 mM to about 1M.

3. A composition, according to claim 1, wherein said tyrosinase is present at a concentration of about 50 to about 5000 U/ml.

4. A method of tanning the human epidermis which comprises applying to said epidermis a composition comprising a cosmetic base in the form of a lotion, a cream or an ointment, an effective amount of a dye precursor selected from the group consisting of tyrosine, 3,4-dihydroxy phenylalanine (dopa), D-dopa, catechol, 5-hydroxyindole, tyramine, dopamine, m-aminophenol, o-aminophenol, p-aminophenol, 4-aminocatechol, 2-hydroxyl-1,4-naphthaquinone (henna), 4-methyl catechol, 3-methyl catechol, 3-isopropyl 6-methyl catechol, 3,4-dihydroxybenzylamine, 3,4-dihydroxybenzoic acid, 1,2-dihydroxynaphthalene, gallic acid, resorcinol, 2-chloroaniline, p-chloroanisole, 2-amino-p-cresol, 4,5-dihydroxynaphthalene 2,7-disulfonic acid, o-cresol, m-cresol, p-cresol, or other related melanin precursors or analogs which are capable of being oxidized to tan, brown or black compounds capable of dyeing the skin distributed through said base, and an effective amount of tyrosinase.

5. A method, according to claim 4, wherein said dye precursor is present at a concentration of about 10 mM to about 1M.

6. A method, according to claim 4, wherein said tyrosinase is present at a concentration of about 50 to about 5000 U/ml.

* * * * *

UNITED STATES PATENT AND TRADEMARK OFFICE
CERTIFICATE OF CORRECTION

PATENT NO. : 4,515,773
DATED : May 7, 1985
INVENTOR(S) : Walter C. Herlihy

It is certified that error appears in the above-identified patent and that said Letters Patent are hereby corrected as shown below:

Col. 2, line 16, that portion reading "O-cresol" should read--o-cresol--.

Col. 3, line 29, that portion reading "2-hydroxy-" should read--2-hydroxyl- --.

Signed and Sealed this

Twentieth Day of August 1985

[SEAL]

Attest:

DONALD J. QUIGG

Attesting Officer  Acting Commissioner of Patents and Trademarks